United States Patent [19]
Ratti et al.

[11] Patent Number: 4,965,355

[45] Date of Patent: Oct. 23, 1990

[54] PROCESS FOR THE PREPARTION OF CEFATRIZINE 1,2-PROPYLENE GLYCOLATE

[75] Inventors: Luigi Ratti, Bergamo; Leone Dall'Asta, Pavia, both of Italy

[73] Assignee: Biochimica OPOS SpA, Milan, Italy

[21] Appl. No.: 314,025

[22] Filed: Feb. 23, 1989

[30] Foreign Application Priority Data

Feb. 24, 1988 [IT] Italy .................. 19513 A/88

[51] Int. Cl.$^5$ .................................. C07D 501/04
[52] U.S. Cl. .................................. 540/226
[58] Field of Search ............ 540/226, 227, 221

[56] References Cited

U.S. PATENT DOCUMENTS 3,970,651  7/1976  Kaplan et al. ............... 540/226

*Primary Examiner*—Nicholas S. Rizzo
*Attorney, Agent, or Firm*—Armstrong, Nikaido, Marmelstein, Kubovcik & Murray

[57] ABSTRACT

Cefatrizine 1,2-propylene glycolate is prepared by reacting p-hydroxyphenylglycine chloride hydrochloride with 7-amino-3-iodomethyl-3-cephem-4-carboxylic acid, and then reacting the thus obtained novel intermediate, 7-[D(−)-α-amino-α-(p-hydroxyphenyl)-acetamido]-3-iodomethyl-3-cephem-4-carboxylic acid, with the sodium salt of 1,2,3-triazol-4(5)-thiol in 1,2-propylene glycol. The addition of water to the reaction mixture causes the cefatrizine, 1,2-propylene glycolate to precipate.

5 Claims, No Drawings

PROCESS FOR THE PREPARTION OF CEFATRIZINE 1,2-PROPYLENE GLYCOLATE

The present invention relates to a process for the preparation of 7-[D(—)-α-amino-α-(p-hydroxyphenyl)acetamido]-3-(1,2,3-triazol-4(5)-yl-thiomethyl)-3-cephem-4-carboxylic acid 1,2-propylene glycolate and to the novel intermediates utilized in that process.

BACKGROUND OF THE INVENTION

7-[D(—)-α-amino-α-(p-hydroxyphenyl)acetamido]-3-(1,2,3-triazol-4(5)-yl-thiomethyl)-3-cephem-4-carboxylic acid is a synthetic cefalosporin, active by the oral route, to which the International Non-Proprietary Name (INN) "cefatrizine" has been given. Cefatrizine, represented by the formula:

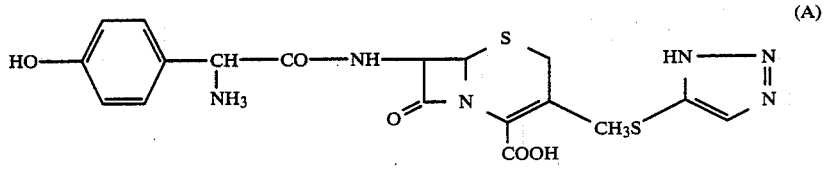

has the drawback of being poorly stable and requires careful handling in its preparation and of the pharmaceutical formulations containing it.

German Patent Application DE No. 2,500,386 discloses the adduct of cefatrizine with 1,2-propylene glycol, hereinafter called "cefatrizine propylene glycolate", and represented by the formula:

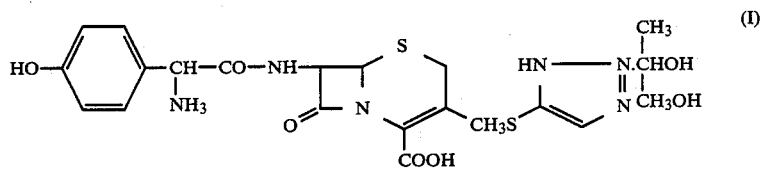

This derivative solves the problems related to the instability of cefatrizine and, moreover, exhibits improved pharmacological kinetics with respect to cefatrizine.

According to the above-identified application, cefatrizine propylene glycolate is prepared directly from cefatrizine, or from its methanolate, by reaction with 1,2-propylene glycol. Cefatrizine is first synthesized by reaction of 7-amino-3-(1,2,3-triazol-4(5)-yl)thiomethyl-3-cephem-4-carboxylic acid having the formula:

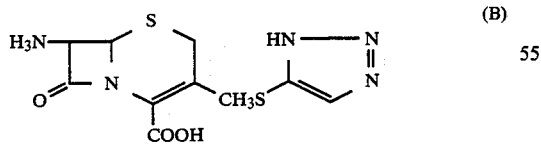

with a reactive derivative of D(—)-p-hydroxyphenylglycine. Compound (B) was silylated prior to reaction, as described in the German Patent Application No. 2,364,192.

In the industrial preparation of cefatrizine propylene glycolate a double solvatation is carried out: first with methanol and then with 1,2-propylene glycol. When using this method, the pH must be adjusted, up to a value of about 4, before isolation of product.

BRIEF DESCRIPTION OF THE INVENTION

It has been now found that cefatrizine propylene glycolate can be readily obtained by direct synthesis starting from 7-amino-3-iodomethyl-3-cephem-4-carboxylic acid by reacting this compound with D(—)-p-hydroxyphenylglycine chloride hydrochloride, isolating the novel intermediate compound, 7-[D(—)-α-amino-α-(p-hydroxyphenyl)-acetamido]-3-iodomethyl-3-cephem-4-carboxylic acid and converting the latter into cefatrizine propylene glycolate by reaction with the sodium salt of 1,2,3-triazole-4(5)-thiol.

It has been found that, according to this method, the cefatrizine propylene glycolate can be isolated by simple dilution with water of the final reaction mixture, without adjusting the pH value, since the pH of the mixture is already 3.8–4.0, corresponding to the isoelectric point of the antibiotic.

DETAILED DESCRIPTION OF THE INVENTION

Thus, the present invention relates to a process for the preparation of cefatrizine propylene glycolate of formula I which comprises:

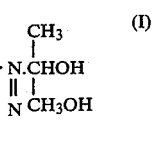

(a) reacting 7-amino-3-halomethyl-3-cephem-4-carboxylic acid of the formula:

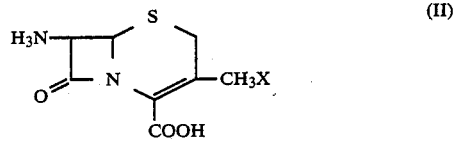

wherein X is chlorine or iodine, with D(—)-p-hydroxyphenylglycylchloride hydrochloride of formula:

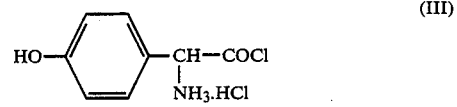

to obtain 7-[D(—)-α-amino-α-(p-hydroxyphenyl)acetamido]-3-halomethyl-3-cephem-4-carboxylic acid of formula:

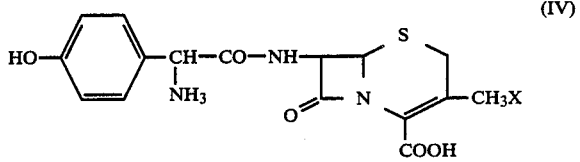

wherein X is a chlorine or iodine; when, in compound of the formula IV, X is chlorine, the thus obtained product is treated with a iodine donor compound;

(b) isolating the compound of formula IV, in which is X is iodine;

(c) reacting the latter compound with the sodium salt of 1,2,3-triazol-4(5)-thiol of formula

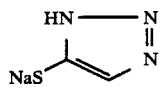

in 1,2-propylene glycol; then (d) adding water to the reaction mixture and isolating the product thus precipitated.

Step (a) of the process of the present invention is preferably carried out in the presence of a silylating agent such as trimethylchlorosilane, mono-trimethylsilylacetamide, bis-trimethylsilylacetamide, hexamethyldisilazane, bis-trimethylsilylurea or their mixtures in an organic solvent such as methylene chloride. In this manner the starting compound of formula II is solubilized and activated by the silylating agent.

The condensation with D(−)-p-hydroxyphenyl-glycylchloride hydrochloride is carried out in the presence of N,N-dimethylaniline or of 4-(N,N-dimethylamino)-pyridine at a low temperature, preferably at from −15° C. to −20° C.

When X is chlorine in the starting compound of formula II, the compound of formula IV, in which X is chlorine, is treated with a iodine donor and is converted in the key intermediate of formula IV, in which X is iodine. Any iodinating compound capable of exchanging a chlorine atom with a iodine atom can used as the iodine donor, for example, the iodide of an alkali metal, preferably sodium iodide.

The compound of formula IV, in which X is iodine, is isolated in step (b) of the process of the present invention according to standard methods, for example, by adding water to the reaction mixture at room temperature and filtering the thus obtained precipitate. The compound can be used without further purification.

In step (c) the compound of formula IV, in which X is iodine, is dissolved in 1,2-propylene glycol, which may contain up to 20% water, and treated with a slight excess of compound V dissolved in water. The reaction is carried out at room temperature (about 20° to 25° C.) for a time which may vary from 30 minutes to 2 hours.

In step (d), water is added to the reaction mixture and the cefatrizine propylene glycolate which precipitates is isolated by simple filtration.

The present invention permits cefatrizine propylene glycolate to be prepared in optimum yields using novel and useful intermediates. Thus, a further feature of the present invention resides in the novel intermediate compounds of the formula IV, among which the iodo derivative (X=iodine) is particularly preferred.

The starting compounds of formula II and III are well known from the literature.

The following non-limiting examples illustrative of the invention:

EXAMPLE 1

(a) A suspension of 0.03 mole of 7-amino-3-iodomethyl-3-cephem-4-carboxylic acid in 120 ml of methylene chloride is added to 0.062 mole of hexamethyldisilazane and 0.55 g of trimethylchlorosilane. The mixture is refluxed for three hours and a clear solution is obtained. After cooling to −20° C., 0.09 mole of N,N-dimethylaniline and then 0.033 mole of D(−)-p-hydroxyphenylglycylchloride hydrochloride, in the form of its hemidioxane solvate, is added. The mixture is stirred at from −15° to −20° C. for 2 hours.

(b) At the end of the reaction, the temperature is permitted to rise to 20° C., and the mixture is treated with 60 ml of water. A solid product is separated, which is filtered, washed with water, then with acetone and dried under vacuum at 30° C. 7-[D(−)-α-amino-α-(p-hydroxyphenyl)acetamido]-3-iodomethyl-3-cephem-4-carboxylic acid of formula IV (X=iodine) in a yield of 88% of the theoretical value is obtained; m.p. 180°–183° C. (dec). Its IR (in KBr) and its 1H-NMR (in DMSO-d) 6 spectra are in agreement with the stated structure.

Analysis for $C_{16}H_{16}N_3IO_5S$ (M.W. 489.289):
Calc. %: C 39.28; H 3.30; N 8.59; I 25.93; S 6.55
Found %: C 39.34; H 3.33; N 9.57; I 25.97; S 6.55.

(c) A solution of 0.015 mole of compound IV (X=iodine) in a mixture comprising 80 ml of 1,2-propylene glycol and 10 ml of water is added to a solution of 0.018 mole of sodium salt of 1,2,3-triazol-4(5)-thiol in 12 ml of water, and the reaction mixture is maintained under stirring for 1 hour at 20° to 25° C.

(d) The reaction mixture is diluted with 55 ml of water, and the product which precipitates is isolated by filtration, washed with a mixture of 1,2-propylene glycol/water (5/1 v/v) and dried under vacuum at 35° C. The cefatrizine propylene glycolate obtained is identical to an authentic sample in a yield of 95%.

EXAMPLE 2

(a) A suspension of 0.03 mole of 7-amino-3-iodomethyl-3-cephem-4-carboxylic acid in 100 ml of dioxane is added to 0.062 mole of hexamethylendisilazane and 0.55 g of trimethylchlorosilane, and the mixture is heated for two and half hours at 35° C. The thus obtained clear solution is cooled to at about 10° C., then 0.09 mole of D-(−)-p-hydroxyphenylglycylchloride hydrochloride as its hemisolvate with dioxane, is added, and the mixture is stirred for 2 hours at from −15° C. to −20° C.

(b) By operating as described in example 1 (b), 7-[D(−)-α-amino-α-(p-hydroxyphenyl)acetamido]-3-iodemthyl-3-cephem-4-carboxylic acid, identical to the compound of the example 1 (b), is obtained in a yield of 90%.

Subsequently, by operating as described in the example 1 (c) and (c), cefatrizine propylene glycolate is obtained in a yield of 95%.

EXAMPLE 3

(a) A suspension of 0.03 mole of 7-amino-3-chloromethyl-3-cephem-4-carboxylic acid in 100 ml of dioxane is added to 0.062 moles of hexamethyldisilazane and the mixture is heated for three hours at 35° C. The thus obtained clear solution is cooled to about 10° C. and then added to 0.09 mole of D-(−)-p-hydroxyphenylglycylchloride hydrochloride, as its hemisolvate with dioxane, and the mixture is stirred for 2 hours at from −15° C. to −20° C. The temperature of the reaction mixture is permitted to rise to 20°–25° C. and the reaction mixture is then treated with 60 ml of water. The solid product which separates is filtered, washed with water then with acetone and dried under vacuum at 30° C. 7-[D(−)-α-amino-α-(p-hydroxyphenyl)-acetamido]-3-chloromethyl-3-cephem-4-carboxylic acid (formula IV, X=chlorine) is obtained in a yield of 89% of the theoretical value; m.p. 161°–164° C. (dec.). Its IR (in KBr) and its $^1$H-NMR (in DMSO-d$_6$) spectra are in agreement with the stated structure.

(b) A solution of 0.3 mole of sodium iodide in 450 ml of acetonitrile is added to 0.3 mole of the thus obtained compound of formula IV (X=chlorine), and the reaction mixture is stirred for 2 hours at room temperature (20°/25° C.). At the end of the reaction, the mixture is poured into 450 ml of water. The precipitate is filtered, washed with water and dried under reduced pressure at 30° C. 7-[D(−)-α-amino-α-(p-hydroxyphenyl-)acetamido]-3-iodomethyl-3-cephem-4-carboxylic acid, identical to the compound of the example 1 (b), is obtained in a yield of 80% of the theoretical value. By operating as described in the example 1 (c) and (d) cefatrizine propylene glycolate is obtained in a yield of 90% of the theoretical value.

We claim:

1. A process for the preparation of cefatrizine 1,2-propylene glycolate which comprises:

(a) reacting a 7-amino-3-halomethyl-3-cephem-4-carboxylic acid of the formula

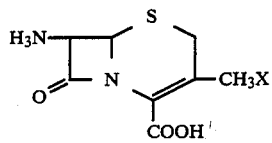

wherein X is chlorine or iodine, with D(−)-p-hydroxyphenylglychylchloride hydrochloride to form a 7-[D(−)-α-amino-α-(p-hydroxyphenyl-)acetamido]-3-halomethyl-3-cephem-4-carboxylic acid of the formula

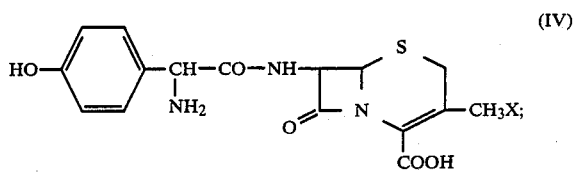

(b) when X is chlorine, reacting the chloro compound with a iodine donor compound to form 7-[D(−)-α-amino-α-(p-hydroxyphenyl)acetamido]-3-iodomethyl-3-cephem-4-carboxylic acid;

(c) reacting 7-[D(−)-α-amino-α-(p-hydroxyphenyl-)acetamido]-3-iodomethyl-3-cephem-4-carboxylic acid with the sodium salt of 1,2,3-triazol-4(5)-thiol in 1,2-propylene glycol; and (d) adding water to the reaction mixture in the previous step and recovering the cefatrizine 1,2-propylene glycolate which precipitates.

2. A process according to claim 1, wherein the D(−)-p-hydroxyphenylglycylchoride hydrochloride is used as its hemi solvate with dioxane.

3. A process according to claim 1, wherein X is iodine.

4. A process according to claim 1, wherein X is chlorine and sodium iodide is used as the iodine donor.

5. A process according to claim 1, wherein the 1,2-propylene glycol contains up to 20% of water.

* * * * *